US006828138B1

(12) United States Patent
Nagai et al.

(10) Patent No.: US 6,828,138 B1
(45) Date of Patent: Dec. 7, 2004

(54) RECOMBINANT SENDAI VIRUS VECTOR INCLUDING A GENE ENCODING A CHEMOKINE

(75) Inventors: Yoshiyuki Nagai, Tokyo (JP); Tatsuo Shioda, Tokyo (JP); Chikaya Moriya, Tokyo (JP)

(73) Assignee: DNAVEC Research Inc., Ibaraki (JP)

(*) Notice: Subject to any disclaimer, the term of this patent is extended or adjusted under 35 U.S.C. 154(b) by 0 days.

(21) Appl. No.: 09/132,521

(22) Filed: Aug. 11, 1998

(51) Int. Cl.[7] .......................... C12N 7/01; C12N 15/00; C07H 21/04; A01H 43/04
(52) U.S. Cl. .............................. 435/235.1; 435/320.1; 514/44; 536/23.72
(58) Field of Search .......................... 435/320.1, 69.1, 435/334, 325; 530/808; 424/93.1, 93.21; 514/44

(56) References Cited

FOREIGN PATENT DOCUMENTS

| EP | 0863202 A1 | 9/1998 | |
|---|---|---|---|
| EP | 0864645 A1 | 9/1998 | |
| WO | WO 9716539 | * 5/1997 | ............ C12N/7/01 |

OTHER PUBLICATIONS

Shido et al. AIDS Research Newsletter, 11: 167, abstract 147, 1997.*
Hasan et al. J. Gen. Vir., 78:2813–2820, 1997.*
Amara et al. J. Exp. Med 86(1):139–146, 1997.*
Kinter et al. PNAS 93:14076–14081, 1996.*
Walker et al. WO 94/08022, Apr. 14, 1994.*
Deonarain et al. Exp. Opin. Ther. Patents. 8(1): 53–69, 1998.*
Crystal, R.G. Science. 270: 404–410, 1995.*
Bleul et al. Nature. 382: 829–833, Aug. 1996.*
Hasan et al. J Gen. Virology. 78(11): 2813–2820, Nov. 1997.*
Yu et al. Genes Cells. 2(7): 457–66, Jul. 1997.*
Calain et al. J of Virology. 67(8): 4822–4830, Aug. 1993.*
Bangham et al. Lancet. 350: 1617–1621, Nov. 1997.*
Miller et al. FASEB. 9:190–199, 1995.*
Anderson et al. Nature. 392: 25–30, Apr. 1995.*
Eck et al. Chap 5. Goodman & Giliman's Pharmacological Basis of Therapeutics. McGraw Hill: NY. p. 77–101, 1995.*

Verma et al. Nature. 389: 239–241, Sep. 1997.*
Kato et al, "The Paramyxovirus, Sendai Virus, V Protein Encodes a Luxury Function Required for Viral Pathogenesis," *The EMBO Journal*, 16:3 578–587 (1997).
Kato et al, "Initiation of Sendai Virus Multiplication From Transfected cDNA or RNA with Negative or Positive Sense," *Genes to Cells*, 1:569–579 (1996).
Kurotani, et al., "Sendai Virus C Proteins are Categorically Nonessential Gene Products but Silencing Their Expression Severely Impairs Viral Replication and Pathogenesis," *Genes to Cells*, 3:111–124 (1998).
Moriya, et al., "Large Quantity Production With Extreme Convenience of Human SDF–1α and SDF–1β by a Sendai Virus Vector," *FEBS Letters*, 425:105–111 (1998).
Tashiro, et al., "Signal Sequence Trap: A Cloning Strategy for Secreted Proteins and Type I Membrane Proteins," *Science*, 261:600–602 (1993).
Yu et al., "Sendai Virus–Based Expression of HIV–1 gp120: Reinforcement by the V(–) Version," *Genes to Cells*. 2 457–466 (1997).
Czaplewski et al., "Identification of Amino Acid Residues Critical for Aggregation of Human CC Chemokines Macrophage Inflammatory Protein (MIP)–1α MIP–1β and RANTES. Characterization of Active Disaggregated Chemokine Variants," *Journal of Biological Chemistry*, 274:16077–16084 (1999).
De Wet et al., "Firefly Luciferase Gene: Structure and Expression in Mammalian Cells," *Molecular and Cellular Biology* 7:725–737 (1987).
Herbst et al., "Folding of Firefly (*Photinus pyralis*) Luciferase: Aggregation and Reactivation of Unfolding Intermediates." *Biochemistry* 37:6586–6597 (1998).
Yonemitsu et al., "Efficient gene transfer to airway epithelium using recombinant Sendai virus." *Nature Biotechnology* 18:970–973 (2000).
Yu et al., "Virus–Mediated Expression of Firefly Luciferase in the Parasitic Protozoan *Giardia lamblia,*" *Molecular and Cellular Biology* 15:4867–4872 (1995).

* cited by examiner

*Primary Examiner*—Joseph Woitach
(74) *Attorney, Agent, or Firm*—Clark & Elbing LLP

(57) ABSTRACT

A recombinant Sendai virus vector expressing chemokine is provided. This vector enables large quantity production of clinically useful chemokines. It is also useful for treatment of diseases that can be treated by chemokines.

19 Claims, 4 Drawing Sheets

A

B

RECOMBINANT SENDAI VIRUS VECTOR INCLUDING A GENE ENCODING A CHEMOKINE

FIELD OF THE INVENTION

This invention relates to a recombinant Sendai virus vector expressing chemokine. More specifically, it relates to a recombinant Sendai virus vector expressing CXC-chemokine. This invention also relates to a method of producing the vector, a pharmaceutical composition comprising it, and a method of inhibiting human immunodeficiency virus (HIV) infection using it.

BACKGROUND OF THE INVENTION

Sendai virus is a non-segmented negative strand RHA virus in the family Paramyxoviridae. Sendai virus has been known as a biotechnologically useful virus, being widely utilized, especially for the production of heterokaryons and hybrid cells, by taking advantage of viral cell-fusion capacity. Also, Sendai virus-based cell fusing liposomes as a vehicle to deliver foreign genes into cells have being developed. Sendai virus has both infectivity and disseminative capability. In contrast, not only genomic negative strand but also antigenomic positive strand of Sendai viral RNA artificially transcribed in vitro cannot serve as a functional template to form infectious virions when transfected into cells. Recently, a system for efficient reconstitution of viral particles from Sendai viral cDNAs has been established, enabling the gene manipulation of Sendai virus to produce a recombinant Sendai virus (W097/16539, Kato, A. et al., Genes to Cells (1996) 1, 569–579).

Chemokines are basic polypeptides capable of binding to heparin and have leucocyte migration enhancing activity and leucocyte activating activity. Chemokines and chemokine receptors are involved in various biological functions, including human immunodeficiency virus infection, inflammation, and immunoreaction.

There are four subfamilies of chemokines, CXC-, CC-, C-, and CX3C-chemokines, based on the first two cysteine residues. Of the CXC-chemokine subfamily, chemokines having an ELR (Glu-Leu-Arg) motif, such as IL-8, Gro α, Gro β, Gro γ, NAP-2, ENA-78, and GCP-2, are potent angiogenic factors, while those with no ELR motif inhibit angiogenesis (Strieter, R. M., J. Biol. Chem. 270, 27348–27357 (1995)). Such chemokines can be used for treat tumors by expressing a chemokine-encoding gene in excess in tumor cells. Furthermore, expression of chemokines in dendritic cells and existence of their receptors have been recently reported (Legler, D. F., J. Exp. Med. 187, 655–660 (1998)). This suggests that cbemokines may be involved in immunological maturation of various T-cells. The CXC chemokines, SDF-1α and SDF-1β, are known to inhibit replication of T-cell line tropic HIV, and CC chemokines, MIP-1α and MIP-1β, and RANTES, inhibit macrophage tropic HIV strains.

SDF-1 is suggested to have the most potent T-cell chemotactic activity and the most potent T-cell adhesion inducing activity (Campell et al., Science 279, 381–382 (1998)). It promotes adhesion of thymocytes of the different differentiation stages to tissues and regulates their distribution in the thymus.

These facts suggest that chemokines, particularly SDF-1, can accelerate establishment of immunity modulated by T-cells and can be used to regulate enhancement of immunity against cancer and effects of vaccines.

In general, recombinant highly basic polypeptides or peptides such as chemokines are produced in *Escherichia coli* with low productivity. Furthermore, *E. coli*-based production generally requires extensive, multi-step purification of the product before use, and therefore is not always feasible for testing many different, genetically engineered derivatives. Extensive aggregation is often inevitable particularly for such basic polypeptides as chemokines. Thus, chemical synthesis of the original and modified versions has been adopted. This approach is not only laborious, including careful refolding, but also expensive. Purification of recombinant chemokines produced in mammalian and other higher vertebrate cells by recombinant viruses has not been reported.

SUMMARY OF THE INVENTION

An objective of this invention is to provide a method of producing recombinant pharmaceutically useful chemokines in large quantity. Another objective of the present invention is to provide a system to produce recombinant chemokines and its medical use.

In order to achieve the above objective, the present inventors made attempts to create recombinant Sendai virus expressing chemokines and found that the recombinant virus produced and accumulated the chemokines expressed in large quantity.

Thus, the present invention provides a recombinant Sendai virus vector expressing chemokine.

The present invention also provides a method of producing chemokine, which comprises inserting at least one chemokine gene into a Sendai virus vector, allowing the vector to produce chemokine, and recovering chemokine.

Furthermore, the invention provides a method of treating human immunodeficiency virus infection, which comprises administering to human subjects a recombinant Sendai virus vector expressing CXC- and CC-chemokines and allowing the vector to express the chemokine in vivo. It also provides a method of treating human immunodeficiency virus infection, which comprises collecting cells from human subjects, infecting the cells with a recombinant Sendai virus vector expressing the chemokine, and giving the infected cells back to the human subjects.

BRIEF DESCRIPTION OF THE DRAWING

FIG. 1 shows construction of the plasmids pSeV/SDF-1α (−) and pSeV/SDF-1β(−) (SEQ ID NO:3) which generate recombinant SeV/SDF-1α and SeV/SDF-1β antigenomic RNAs, respectively. pT7 stands for the T7 promoter; N, P, M, F, HN, and L for Sendai virus structural genes N, P, M, F, HN, and L, respectively; Rbz for the hepatitis delta virus ribozyme; E for the stop signal; and S for the restart signal.

FIGS. 2A and 2B shows chemotactic activity of SDF-1α produced from a recombinant Sendai virus (rSeV). In FIG. 2A, ○ stands for the culture supernatant of SeV/SDF-1α and ● for that of wild-type Sendai virus. Error bars indicate standard deviations of duplicated data. in FIG. 2B, □ stands for SDF-1α and ■ for SDF-1β derived from the respective rSeVs.

FIG. 3 shows anti-HIV activity of SDF-1α and SDP-1β. □ stands for SDF-1α, ■ for SDF-1β, and ▲ for cultures which were not treated with chemokines.

FIG. 4 shows an inhibitory effect of SDF-1α on cell fusion mediated by gp160 of HIV-1 strain NL43. Filled and hatched bars indicate β-galactosidase activity within cells treated with the culture supernatants of CEF infected with wild-type Sendai virus and SeV/SDF-1α, respectively.

DETAILED DESCRIPTION OF THE INVENTION

Figure 1:
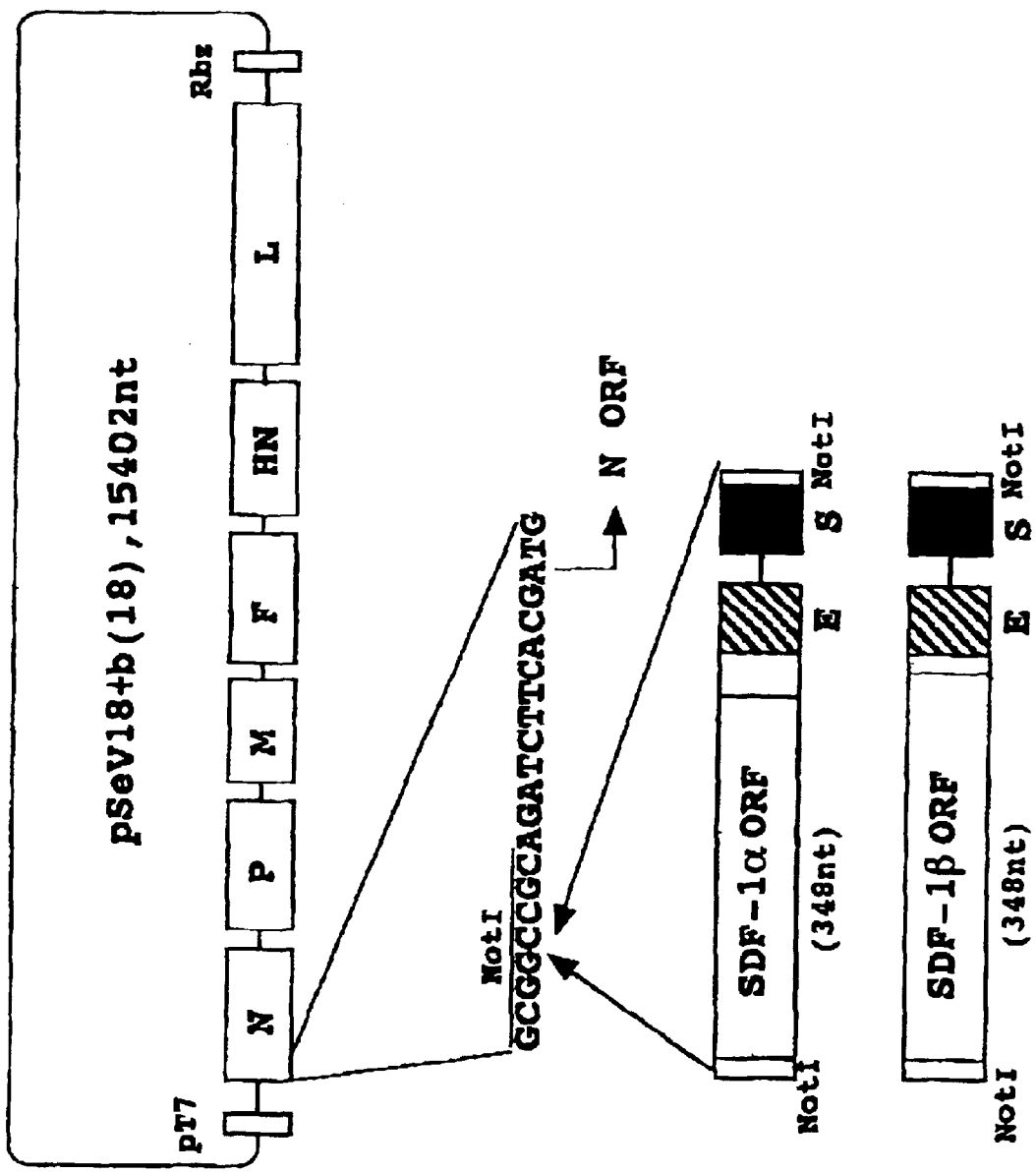
Figure 2:
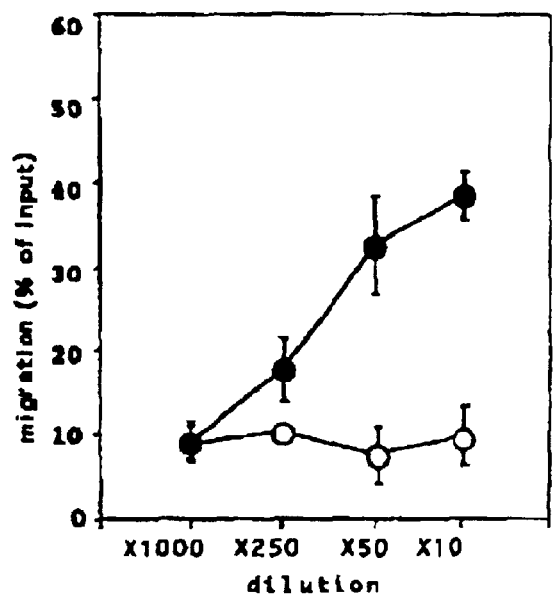
Figure 2:
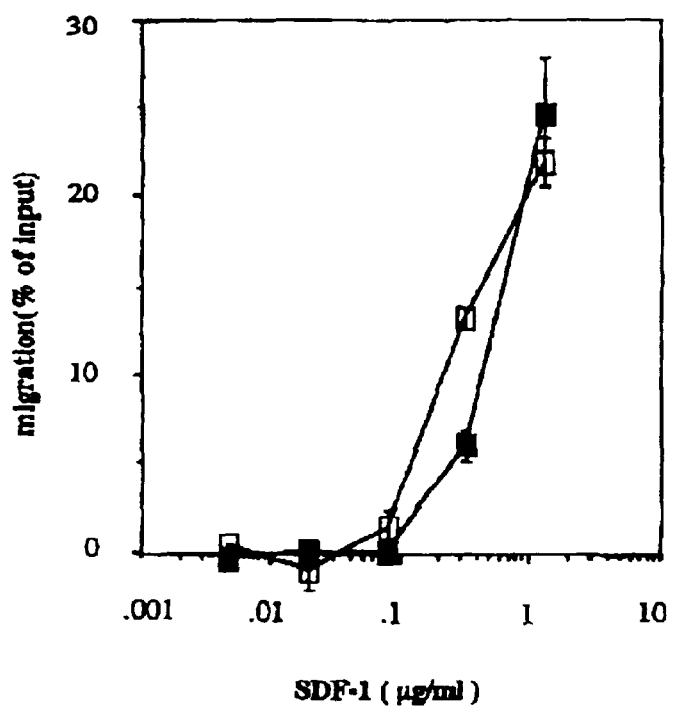
Figure 3:
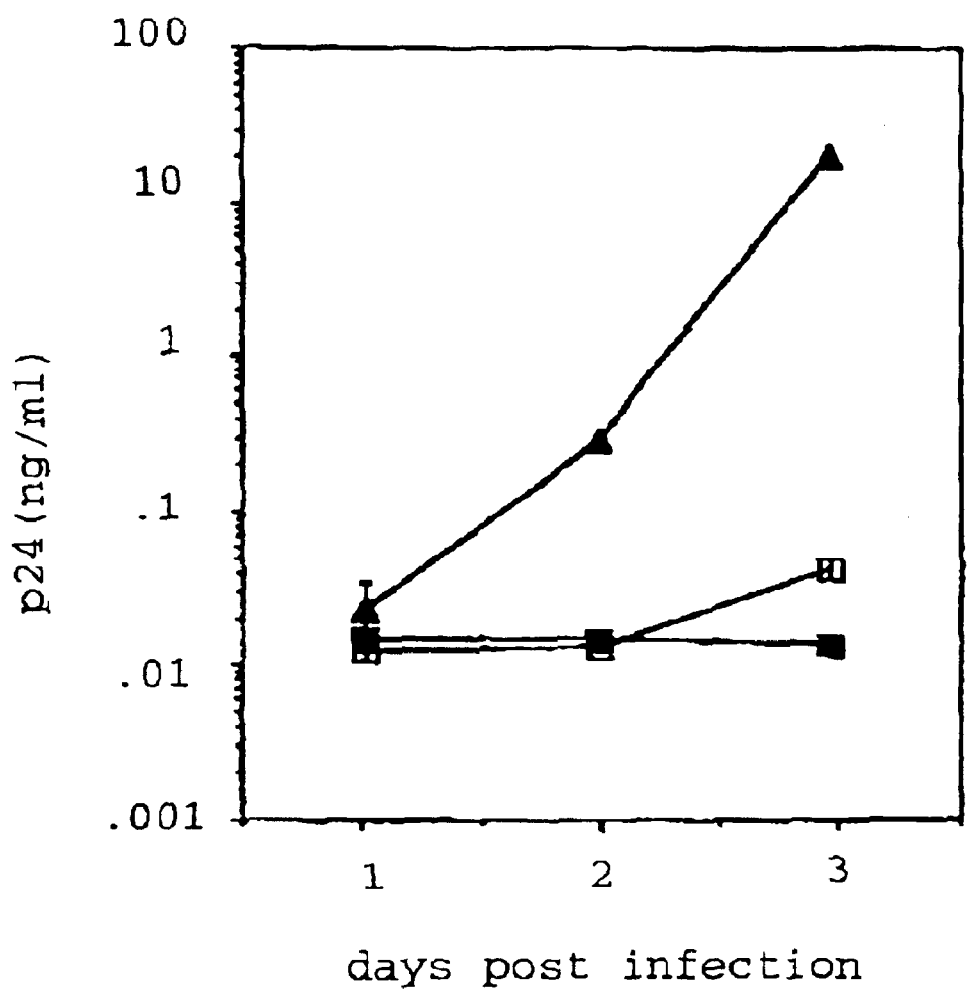

The term "infectivity" used herein means the capability of a virus to transfer its nucleic acid, etc. into cells through its adhesiveness to cells and penetrating capability into cells via various mechanisms including fusion of the viral membrane and host cellular membrane. The term "disseminative capability" used herein means the capability to form infectious particles or their equivalent complexes and disseminate them to other cells following the transfer of nucleic acid into host cells by infection or artificial techniques and the intracellular replication of said nucleic acid.

Chemokines to be expressed in a Sendai virus vector in this invention are not particularly limited as long as they are pharmaceutically useful. About thirty chemokines have been identified so far. Of the four chemokine subfamilies (CXC, CC, C, and CX3C), CXC- and CC-chemokines are preferably used in this invention. Examples of CXC-chemokines include IL-8, Gro/MGSA, NAP-2, ENA-78, GCP-2, PF4, IP-10, Mig, SDF-1/PBSF, H174, and BLC/BCA-1. Examples of CC-chemokines include MIP-1α, MIP-1β, RANTES, and MCP-1. Nucleotide sequences encoding these chemokines are known and can be obtained as described in, for IL-8, Yoshimura et al., Proc. Natl. Acad. Sci. USA 84, 9233–9237 (1987) and Matsushima, K. et al., J. Exp. Med. 167, 1883–1896 (1988); for SDF-1/PBSF, Tashiro, K. et al., Science 261, 600–603 (1993).

It is suggested that IL-8 is involved in dermatitis (Harada, A. et al., Int. Immunol. 5, 681–690 (1993)), arthritis (Akaboshi, T. et al., Lymphokine Cytokine Res., 13, 113–116 (1994)), acute nephritis (Wada, T. et al., J. Exp. Med. 180, 1135–1140 (1994)), pulmonary ischemic reperfusion injury (Sekido, M. et al., Nature 365, 654–657 (1993)), cerebral embolic ischemia (Matsumoto et al., Lab. Invest. 77, 1119–1125 (1997)), and specific leucocyte infiltration (Lu, B. et al., J. Exp. Med. 187, 601–608 (1988)); PF4 is involved in activation of integrin in platelet and angiopathy by adhesion to endothelium (Springer, T. A. et al., Annu. Rev. Physiol. 57, 827–872 (1995)); IP-10 is involved in antitumor effect of IL-12 (Yu, WG et al., J. Leukocyte Biol. 62, 450–457 (1997)); Mig is involved in accumulation of activated T cells at inflammatory sites of the vicinity of carcinomas, delayed hypersensitive skin, and experimental autoimmune encephalomyelitis (Springer, T. A., Annu. Rev. Physiol. 57, 827–872 (1995); SDF-1/PBSF inhibits T cell tropic HIV infection and MIP-1α, MIP-1β, and RANTES, macrophage tropic strains (D'Souza, M. P. et al., Nature Med. 2, 1293–1300 (1996) and Coffey, M. J. et al., Am. J. Physiol. 272, 5 Pt 1, L1025-9 (1997)). The recombinant Sendai virus expressing these chemokines can be used for treating the diseases as described above. In particular, stromal cell-derived factors 1 α and (SDF-1α and SDF-1β), MIP-1α, and MIP-1β, which are known to inhibit HIV replication, are preferably used.

Sendai virus, the starting material in the present invention for the insertion of a chemokine gene, may be a strain classified to parainfluenza virus type I, exemplified by Sendai virus Z strain or Fushimi strain. Furthermore, incomplete viruses such as DI (defective interfering) particles, synthetic oligonucleotides, etc. may be used partial materials. Examples of the Sendai virus vector used in the present invention include pUC18/T7(+)HVJRz.DNA, pUC/T7(−)HVJRz.DNA (both described in WO97/16539), and pSeV18+b(+) (Yu, D. et al., Genes to Cells 2, 457–466 (1997)).

So far as the recombinant Sendai virus of the present invention can produce a desired chemokine, any genome gene may be deleted or modified. In the Sendai viral RNA, it is preferable to insert a sequence of a multiple of 6 nucleotides in length between the sequences R1 and R2 [Journal of Virology, Vol. 67, No. 8 (1993) p.4822–4830 and genbank M30202]. Levels of expression of a chemokine gene inserted into a vector can be regulated by virtue of the site of gene insertion and the base sequences flanking the chemokine gene. For example, in the case of Sendai viral RNA, it is known that there are increasing levels of expression of the inserted gene with decreasing distance of the gene from the promoter at the 3' terminus.

Also, part of genes related with RNA replication of Sendai virus may be modified to, for example, maintain vector's expression capability, inactivate genes for immnogenicity, improve safety, or enhance the efficiency of RNA transcription and replication. Concretely, for example, at least one of the replication factors, the NP, P/C and L proteins may be modified to enhance or reduce the transcription and replication capabilities. The HN protein, one of the structural proteins, has dual activities as hemagglutinin and neuraminidase. For example, the reduction of the former activity say increase the viral stability in blood stream, and viral infectivity can be regulated by modifying the latter activity or replacing the envelop protein with that of the other viruses (J. Virol. (United States) 72(6), 5296–5302 (1998)). Also, the modification of the F protein mediating membrane fusion may be useful for improving membrane fusion liposomes constructed by fusing the reconstituted Sendai virus and artificial liposomes enclosing a desired drug or gene. Furthermore, part of the viral gene can be mutated or deleted to suppress replication of the virus vector in vivo to thereby enhance the safety of the vector. For example, a Sendai virus variant, which does not express C and C' proteins, but does express Y1 and Y2 proteins, is known to impair both gene expression and genome replication (Kurotani, A. et al., Genes to Cells 3, 111–124 (1998)). Also, deletion of V protein attenuates in vivo pathogenicity (Kato, A. et al., The EMBO Journal 16(3), 578–587 (1997)).

When it is not preferable to use the virus vector having the disseminative capability in gene therapy, the recombinant Sendai virus vector that is infectious, replicates autonomously, and is not disseminative can be used. This vector can be constructed in accordance with the method described in WO97/16583, which is incorporated herein by reference.

Specifically, once an RNA molecule containing a foreign gene transcribed from "specific viral cDNA deficient in at least a part of structural genes but normal in genes coding for N, P, and L begins to be replicated by N, P, and L coexpressed by the cotransfected plasmid cDNAs, a virus particle will be formed, which is infectious to and autonomously replicating in a new cell and can express the foreign gene, but deficient in the disseminative potency. In the case of Sendai virus, "the genes related to autonomous replication" refer to the NP, P and L genes, and "the gene related to the disseminative capability" refers to any one of the M, F and HN genes. Therefore, the RNA molecule of Sendai virus deficient in one or more of the above genes related to the disseminative capability, for example, is suitable as a component contained in the "complex" of the present invention. Also, the RNA molecule having all the M, F and HN genes deleted or inactivated are also preferable as the component contained in the "complex" of the present invention. On the other hand, it is necessary for the genes encoding the NP, P and L proteins to be expressed from RNA. However, the sequences of these genes are not necessarily the same as those of virus, and may be modified by introducing mutation, substitution, deletion, addition of nucleotide(s), or replacing by the corresponding gene derived from other viruses, so far as the transcription and replication activity of the resulting RNA is similar to or higher than that of the natural one.

Recombinant Sendai viral vectors of the present invention can be obtained, for example, by in vitro transcribing the recombinant cDNA encoding the gene-technologically produced recombinant Sendai viral vector genome, producing the recombinant Sendai viral genome RNA, and introducing said RNA to a host simultaneously expressing the NP, P, and L proteins (each protein may be a protein with an equivalent activity) of Sendai virus. Alternatively, Sendai viral vectors of the present invention can be obtained by introducing a) the recombinant cDNA coding for the gene-technologically produced recombinant Sendai viral vector genome, and b) a unit capable of intracellularly transcribing RNA with the DNA as template into a host simultaneously expressing the NP, P, and L of Sendai virus. In this case, the recombinant cDNA a) may be inserted downstream of a specific promoter, and the transcription unit b) may be a DNA molecule expressing a DNA-dependent RNA polymerase acting on the specific promoter.

When a chemokine gene is inserted into a plasmid for expressing the negative strand Sendai viral RNA, it is necessary to insert the gene downstream of the promoter in an orientation for transcribing an antisense RNA of the chemokine gene.

Preferred hosts for expressing chemokines may be any cells susceptible to the infection by the recombinant Sendai virus. Cell lines used as hosts in the present invention includes LLCMK2, MDCK, MDBK, CV-1, Hela, HepG2, P19, F9, CHO, PC12, 293cell, BAF3, Jerkat, Human PBMC, MT-4, Molt-4, NIH3T3, L929, chicken embryo fibroblasts (CEF). Of these, CV-1 and further, CEF are preferably used.

It is possible to efficiently produce a chemokine gene product by infecting these hosts with the recombinant Sendai virus integrated with an expressible chemokine gene, incubating the infected cells to allow them to express the chemokine gene, and recovering the chemokine produced. These procedures can be performed by known methods. One skilled in the art would readily determine appropriate methods and conditions for the procedures.

The thus-recovered crude chemokines can be purified simply by, for example, removing the Sendai virus by centrifugation and subjecting to known biochemical purification method such as affinity chromatography, depending on the chemokine produced.

The recombinant Sendai virus vector expressing chemokine of the present invention can be used for treatment of diseases that can be treated by chemokines. The nondisseminative virus vector of the present invention derived from Sendai virus can be highly safe in the clinical application. Further, the Sendai virus vector having the disseminative capability can be therapeutically effective with a relatively small dosage. The recombinant Sendai virus vector of the present invention can produce chemokine efficiently. For example, the recombinant Sendai virus vector expressing SDF-1α or SDF-1β can effectively inhibit HIV relplication.

The pharmaceutical composition of the present invention comprises the recombinant Sendai virus vector of the present invention and a pharmaceutical carrier such as physiological saline (PBS) or a pharmaceutical acceptable medium. The composition may further contain other additives having low immunogenicity. Examples of the additives include low molecular weight amino acids, such as arginine, glutamic acid, or serine, and their derivatives, carbohydrates such as glucose, inositol, lactose, mannitol, sorbitol, trehalose, or xylose, and their derivatives.

The nondisseminative recombinant Sendai virus vector of the present invention can be used for gene therapy ex vivo or in vivo. The ex vivo method can be performed by collecting target cells from human subjects, infecting the cells with the rSeV, and giving the infected cells back to the human subjects. The in vivo method can be performed by administering the virus vector to human subjects.

The dose of the virus vector varies depending on the age, weight, and symptoms of the patients, the administration route, and the kinds of chemokines. The virus vector is administered at 0.1 to 10,000 virions/cell, preferably 0.5 to 50 virions/cell.

In the following, the present invention will be concretely described with reference to Examples, but is not limited to these Examples.

EXAMPLE 1

Materials

HIV-1 strains NL43 (Adachi, A. et al., (1986) J. Virol. 59, 284–291), SF33 (York-Higgins, D. et al., (1990) J. Virol. 64, 4016–4020), TK11 (Oka, S. et al., (1994) AIDS Res. Hum. Retroviruses 10, 271–277), and SIV mac strain 239 (Naidu, Y. M. et al., (1988) J. Virol. 62, 4691–4696) were grown in MT4 T cell line. HIV-1 strain SF 162 (Shioda, T. et al., (1991) Nature (Lond.) 234, 167–169), primary isolates #12, #15, and #37 (Shioda, T. et al., (1997) J. Virol. 71, 4871–4881) were propagated in phytohemagglutinin-stimulated peripheral blood mononuclear cells (PBMC). CV1 cells were grown in minimum essential medium (MEM) supplemented with 10% fetal bovine serum (FBS). MT4 cells were grown in RPMI-1640 supplemented with 10% FBS. Primary chicken embryo fibroblasts (CEF) were prepared as described in Hanafusa, H. (1969) Proc. Natl. Acad. Sci. USA 63, 318–325, and maintained in MEM supplemented with 10% FBS. After virus infection, CEF were maintained in MEM without serum. PBMC from healthy seronegative donors were prepared and grown as described in Shioda, T. et al., (1997) J. Virol. 71, 4871–4881.

Generation of a Recombinant Sendai Virus Carrying Human SDF-1 α Gene

The plasmid pSeV18$^+$(+) carries a cDNA copy of Sendai Virus full length antigenome (positive strand RNA), in which an additional 18 synthetic nucleotides containing unique NotI site was inserted within the N gene and just upstream of its open reading frame (ORF) (Hasan et al., J. Gen. Virol. 78, 2813–2820 (1997)).

A 348-bp DNA fragment containing entire coding frame of human SDF-1 α gene (267 bp) followed by a new set of synthetic stop or end (E) (termination/polyadenylation) and restart (S) signals with intervening three nucleotides was amplified with NotI-tagged primers and inserted into the NotI site in pSeV18$^+$(+) generating pSeVSDF-1 α(+) (FIG. 1).

pSeVSDF-1α (+) was transfected to v-TF7-3 infected LLCMK2 cells and the T7-driven full length recombinant Sendai virus RNA genomes were encapsulated with N, P, and L proteins, which were derived from the contransfected respective plasmids. Following a 40-h incubation to allow initiation of the infectious cycle and generation of progeny, the transfected cells were injected into embryonated chicken eggs to amplify the recovered virus. After a successive passage in eggs, the recombinant virus reached a titer of over $10^9$ PFU/ml comparable to that of the wild-type Sendai virus. This second passage, initiated at a dilution of $10^{-6}$, resulted in complete elimination of helper vTF7-3 present in an amount of $10^4$ to $10^5$ PFU/ml. Nucleotide sequencing of the recombinant virus revealed that there was no accidental nucleotide substitution within the inserted SDF-1α gene. The recovered virus was named SeV/SDF-1α. In the same manner, a recombinant Sendai virus expressing SDF-1β (SeV/SDF-1β) was constructed.

EXAMPLE 2

Confirmation of Expression of SDF-1α

Expression of SDF was confirmed by SDS-PAGE, Nothern blot, and Western blot. As a result of SDS-PAGE, a polypeptide with a molecular mass of 8 kDa was observed as a major protein constituent in the culture supernatant of CEF infected with SeV/SDF-1α.

Northern blot was performed as follows. First, total RNA was extracted using RNAzol-B (Tel-Test Inc.) from approximately $10^6$ CEF infected with the SeVSDF-1α(+) at various time points post infection (p.i.). The RNAs were ethanol precipitated, dissolved in formamide/formaldehyde solution, then electrophoresed in 1% agarose-formamide/MOPS gels, and capillary transferred onto Hibond-N filters (Amersham). They were hybridized with the SDF-1 specific NotI fragment from pSeVSDF-1α(+) probes that had been labeled with α-$P^{32}$-dCTP using Multiprime DNA Labeling System (Amersham). As a result, the transcripts specific to SDF-1α with an expected size of approrximately 400 bases were detected.

Western blot was performed as follows. Culture supernatants of infected cells were first electrophoresed in 15% SDS-polyacryamide gels (Laemmli, U.K. (1970) Nature 227, 680–685). The proteins in the gels were electrotransferred onto PVDF membranes (Millipore) and probed with anti-SDF-1 antiserum, which was prepared by immunized rabbits with multiple antigen peptide containing residues 33–45 (RFFESHVARANVK: SEQ ID NO: 1) synthesized by Research Genetics Inc. As control, culture supernatants of wild-type Sendai virus infected cells were used. The SDF-1α transcript was absent in wild-type Sendai Virus infected fluid, and reacted specifically with rabbit serum immunized with 13-mer peptides derived from human SDF-1α sequence.

These results demonstrated that substantial amounts of SDF-1α were produced from the recombinant Sendai Virus and secreted into the culture supernatant. After a 72-h incubation, the amount of SDF-1α in the culture fluid reached over 10 μg/ml.

EXAMPLE 3

Purification of SDF-1α and SDF-1β

Culture supernatant of CEF infected with SeV/SDF-1α or SeV/SDF-1β were harvested 72 h after infection and the SeV viruses were removed by centrifugation at 48,000×g for 1 h at 4° C. The supernatant was applied to an 1 ml Hi-Trap heparin column (Pharmacia) equilibrated with 10 mM sodium phosphate buffer, pH 7.2, on an FPLC system (Pharmacia). After washing with 5 ml of the same buffer, bound proteins were eluted with 10 ml of linear gradient of 0.4 to 1.0 M NaCl in the same buffer. Fractions were diluted more than 80-fold before assaying the chemotactic or anti-HIV activity. Active fractions were collected.

Amino acid sequestering was performed for the purified SDF-1α, demonstrating the $NH_2$-terminal KPVSLSYRX-PXR (SEQ ID NO:2), identical to the reported sequence of SDF-1α. In this NH2-terminal peptide, X should be read as C, because it cannot be resolved by the sequencing method employed.

EXAMPLE 4

Assay of Biological Activities of Recombinant SDF-1α and SDF-1β

1. Chemotactic Assay

Lymphocyte chemotaxis assays were performed according to the method described by Bluel et al. (Bluel, C. C. et al., (1996) J. Exp. Med. 184, 1101–1109). First, human peripheral blood lymphocytes (PBL) were obtained from healthy donors by Ficoll-Histpaque method. Monocytes were removed by 1-h steps of plastic adherence. Cell (5×$10^5$) in 100 μl RPMI-1640 medium containing 0.25% human serum albumin (HSA) were added to the upper chamber of a 5-μm pore polycarbonate Transwell culture insert (Coaster) and incubated with the indicated concentrations of proteins for 3 h. Transmigrated cells were counted with a FACScan (Becton Dickinson) for 20 s at 60 μl/min.

As shown in FIG. 2, the culture fluid efficiently attracted freshly prepared PBL. This means that the recombinant SDF-1α and SDF-1β was functionally authentic.

2. Anti-HIV-1 Assay

PHA-stimulated PBMC or MT4 cells (5×$10^5$) were incubated with indicated concentrations of chemokines for 16 h, and then exposed to 1000 50% tissue culture infective dose of HIV-1 for 2 h at 37° C. The cells were washed with RPMI medium and maintained in the culture medium for each cell type. Culture supernatants of the infected cells were assayed for the levels of p24 core antigen (Abbot). Data points are the means of duplicate cultures. The results are shown in Table 1.

TABLE 1

Effect of SDF-1α on the growth of several HIV-1 and SIV mac strains

| Strain | Phenotype | p24 (ng/ml) Control | SDF-1α (0.5 μg/ml) |
|---|---|---|---|
| NL43[a] | SI/T cell line tropic | 54.44 | 1.40 |
| SF33[a] | SI/T cell line tropic | 78.50 | 6.40 |
| TK11[a] | SI/T cell line tropic | 355.00 | 26.00 |
| #15[b] | SI | 100.23 | 1.36 |
| SF162[b] | NSI/macrophage tropic | 10.43 | 12.35 |
| #12[b] | NSI | 27.91 | 17.70 |
| #37[b] | NSI | 22.01 | 20.00 |
| SIV mac239[a] | T cell line tropic | 4.81[c] | 6.22[c] |

Note: SI and NSI indicate syncytium inducing and non-syncytium inducing phenotype, respectively. Data points are means of duplicate cultures.
[a]Inhibition by SDF-1α in MT4 cells was evaluated at day 3 after infection.
[b]Inhibition by SDF-1α in PBMC cultures was evaluated at day 7 after infection.
[c]SIV mac p27 core antigen levels are shown.

The recombinant SDF-1α suppressed the replication of three different T cell line tropic HIV-1 strains, NL43, SY33, and TK11, in the MT4 T cell line, and one syncytium inducing primary isolate #15 in PBMC culture. The SDF-1α did not suppress the replication of macrophage tropic strain SF162, nor two non-syncytium inducing primary isolates, #12 and #37, in PBMC cultures. The recombinant SDF-1α did not show any inhibitory activity for simian immunodeficiency virus (SIV) strain mac239 in MT4 cells. These results are consistent with the expected specificity of antiviral activities of SDF-1α and thus confirmed the biological authenticity of the Sendai virus-derived recombinant SDF-1α.

Separately, MT4 cells were treated with 200 ng/ml of purified SDF-1α or SDF-1β and then infected with NL43 strain of HIV-1. The levels of p24 core antigen in the culture supernatants were assayed periodically. The results are shown in FIG. 3. Both of SDF-1α and SDF-1β suppressed HIV-1 strain NL43 efficiently.

3. Cell Fusion Assay

A recombinant vaccinia virus-based gene activation assay using a β-galactosidase gene as a reporter was perfumed as described by Nussbaum et al. (Nussbaum et al., (1994) J. Virol. 68, 5411–5422). First, L cells were transfected with plasmid pG1NT7β-gal with DOTAP and then infected with recombinant vaccinia virus expressing gp160 of HIV-1 strain NL43. MT4 cells were infected with vTF7-3 (Fuerst, T. R. et al., (1986) Proc. Natl. Acad. Sci. USA 83, 8122–8126), and then treated with SeV/SDF-1α or wild-type Sendai virus. After 16-h incubation at 31° C., equal numbers ($1\times10^5$) of L and MT4 cells were mixed and incubated at 37° C. for 3 h. β-galactosidase activity within cell lysate was measured by using chlorophenol red-β-D-galactopyranoside as a substrate.

Figure 4:

The results shown in FIG. 4, indicating that the recombinant SDF-1α inhibited the step of membrane fusion.

4. Luciferase Assay

MT4 cells were incubated with or without 0.5 μg/ml of SDF-1α for 16 h and then transfected with 5 μg of the plasmid carrying the luciferase reporter gene under the control of HIV-1 LTR, pHIV-1 LTR/L-A-5'438, and 5 μg of the tat expression plasmid, pcDLSRα/tat501, with DOTAP (Boehringer-Mannheim). Cells were maintained in the presence or absence of 0.5 μg/ml of SDF-1α for additional 40 h and then lysed for luciferase assay (Kato et al., (1996) Genes Cells 1, 569–579).

What is claimed is:

1. A recombinant Sendai virus vector comprising a gene encoding a chemokine, wherein said gene is operatively linked to a functional promoter, wherein said vector, when transfected to a host, expresses the chemokine in a biologically active form.

2. The recombinant Sendai virus vector of claim 1, wherein said chemokine is CXC-chemokine.

3. The recombinant Sendai virus vector of claim 2, wherein said CXC-chemokine is stromal cell-derived factor α or stromal cell-derived factor β.

4. The recombinant Sendai virus vector of claim 3, wherein said vector is disseminative.

5. The recombinant Sendai virus vector of claim 3, wherein said vector is infectious and replicates autonomously, but is not disseminative.

6. A method of producing a biologically active chemokine which comprises the steps of: inserting at least one chemokine gene into a Sendai virus vector, introducing said vector into an isolated host cell, allowing the host to produce said chemokine, and recovering said chemokine from the culture supernatant.

7. The method of claim 6, wherein said chemokine is CXC-chemokine.

8. The method of claim 7, wherein said CXC-chemokine is biologically active stromal cell-derived factor α or biologically active stromal cell-derived factor β.

---

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: synthetic peptide

<400> SEQUENCE: 1

Arg Phe Phe Glu Ser His Val Ala Arg Ala Asn Val Lys
 1               5                  10

<210> SEQ ID NO 2
<211> LENGTH: 12
<212> TYPE: PRT
<213> ORGANISM: Homo sapiens
<220> FEATURE:
<221> NAME/KEY: VARIANT
<222> LOCATION: 9, 11
<223> OTHER INFORMATION: Xaa is predicted to be Cys

<400> SEQUENCE: 2

Lys Pro Val Ser Leu Ser Tyr Arg Xaa Pro Xaa Arg
 1               5                  10

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
gcggccgcag atcttcacga tg                                           22
```

9. The method of claim 8, wherein said host cell expresses Sendai virus virions and the step of recovering comprises the step of removing virions by centrifugation.

10. The method of claim 7, wherein said host cell expresses Sendai virus virions and the step of recovering comprises the step of removing virions by centrifugation.

11. The method of claim 6, wherein said host cell expresses Sendai virus virions and the step of recovering said chemokine from the culture supernatant includes the step of removing virions by centrifugation.

12. A composition comprising a recombinant Sendai virus vector comprising a gene encoding a stromal cell-derived factor chemokine, wherein said gene is operatively linked to a functional promoter, wherein said vector, when transfected to an isolated host cell, expresses biologically active stromal cell-derived factor α or biologically active stromal cell-derived factor β and a carrier, wherein said vector is disseminative.

13. A composition comprising a recombinant Sendai virus vector comprising a gene encoding a stromal cell-derived factor chemokine, wherein said gene is operatively linked to a functional promoter, wherein said vector, when transfected to an isolated host cell, expresses biologically active stromal cell-derived factor α or biologically active stromal cell-derived factor β and a carrier, wherein said vector is infectious and replicates autonomously, but it is not disseminative.

14. An isolated host cell transfected with a recombinant Sendai virus vector expressing a biologically active chemokine.

15. A method of inhibiting proliferation of HIV-infected cells in vitro which comprises, incubating the isolated host cell of claim 14 in vitro under conditions that allow for secretion of biologically active chemokine; and contacting said chemokine with cells that are infected with HIV, wherein said chemokine inhibits proliferation of HIV-infected cells in vitro.

16. The host of claim 14, wherein said chemokine is biologically active CXC-chemokine.

17. The host of claim 16, wherein said CXC-chemokine is biologically active stromal cell-derived factor α or biologically active stromal cell-derived factor β.

18. A method of inhibiting proliferation of HIV-infected cells in vitro which comprises, incubating the host cell of claim 17 in vitro under conditions that allow for secretion of biologically active CXC-chemokine; and contacting said CXC-chemokine with cells that are infected with HIV, wherein said CXC-chemokine inhibits proliferation of HIV-infected cells in vitro.

19. A method of inhibiting proliferation of HIV-infected cells in vitro which comprises, incubating the host cell of claim 16 in vitro under conditions that allow for secretion of biologically active CXC-chemokine; and contacting said CXC-chemokine with cells that are infected with HIV, wherein said CXC-chemokine inhibits proliferation of HIV-infected cells in vitro.

* * * * *

UNITED STATES PATENT AND TRADEMARK OFFICE
CERTIFICATE OF CORRECTION

PATENT NO.    : 6,828,138 B1
DATED         : December 7, 2004
INVENTOR(S)   : Yoshiyuki Nagai et al.

It is certified that error appears in the above-identified patent and that said Letters Patent is hereby corrected as shown below:

Title page,
Item [56], References Cited, OTHER PUBLICATIONS,
"Shido et al." reference, replace "Shido" with -- Shioda --; and
"Eck et al." reference, replace "Giliman's" with -- Gilman's --; and
"Kato et al , "The Paramyxovirus, Sendai Virus, V Protein Encodes a Luxury Function Required for Viral Pathogenesis," reference, replace "Kato et al ," with -- Kato et al., --; and
"Kato et al , "Initiation of Sendai Virus Multiplication From Transfected cDNA or RNA with Negative or Positive Sense," reference, replace "Kato et al ," with -- Kato et al., --.

Column 1,
Line 52, replace "cbemokines" with -- chemokines --.

Column 2,
Line 46, replace "(-) and pSeV/SDF-1β(-)" with -- (+) and pSeV/SDF-lβ (+) --; and
Line 57, replace "in" with -- In --.

Column 3,
Line 30, replace "Akaboshi" with -- Akahoshi --; and
Line 45, after "(1995)" insert --) --.

Column 5,
Line 20, "into a host simultaneously expressing" should begin on line 21; and
Line 63, replace "relplication" with -- replication --.

UNITED STATES PATENT AND TRADEMARK OFFICE
CERTIFICATE OF CORRECTION

PATENT NO.    : 6,828,138 B1
DATED         : December 7, 2004
INVENTOR(S)   : Yoshiyuki Nagai et al.

It is certified that error appears in the above-identified patent and that said Letters Patent is hereby corrected as shown below:

Column 7,
Line 29, replace "approrximately" with -- approximately --; and
Line 63, replace "sequestering" with -- sequencing --.

Column 8,
Line 51, replace "SY33" with -- SF33 --.

Signed and Sealed this

Twenty-sixth Day of April, 2005

JON W. DUDAS
*Director of the United States Patent and Trademark Office*